United States Patent

Suemer

[11] Patent Number: 6,136,033
[45] Date of Patent: Oct. 24, 2000

[54] ARTIFICIAL COTYLOID CAVITY

[75] Inventor: Aykut Suemer, Instanburl, Turkey

[73] Assignee: Stratec Medical AG, Oberdorf, Switzerland

[21] Appl. No.: 09/068,408

[22] PCT Filed: Nov. 8, 1996

[86] PCT No.: PCT/CH96/00395

§ 371 Date: Jul. 6, 1998

§ 102(e) Date: Jul. 6, 1998

[87] PCT Pub. No.: WO97/17040

PCT Pub. Date: May 15, 1997

[51] Int. Cl.[7] .................................................. A61F 2/32
[52] U.S. Cl. ............................................................ 623/22.21
[58] Field of Search .................................. 623/18, 19, 22, 623/23

[56] References Cited

U.S. PATENT DOCUMENTS

| 3,584,318 | 6/1971 | Scales et al. | 3/1 |
| 3,863,273 | 2/1975 | Averill | 3/1 |
| 5,458,649 | 10/1995 | Spotorno et al. | 623/22 |
| 5,549,697 | 8/1996 | Caldarise | 623/22 |
| 5,645,601 | 7/1997 | Pope et al. | 623/22 |

FOREIGN PATENT DOCUMENTS

| 083 708 | 7/1983 | European Pat. Off. . |
| 237 751 | 9/1987 | European Pat. Off. . |
| 242 633 | 10/1987 | European Pat. Off. . |
| 444 382 | 9/1991 | European Pat. Off. . |
| 578 322 | 1/1994 | European Pat. Off. . |
| 655 230 | 5/1995 | European Pat. Off. . |
| 95/01 139 | 1/1995 | WIPO . |
| 95/22 944 | 8/1995 | WIPO . |

Primary Examiner—David J. Isabella
Attorney, Agent, or Firm—Pearne & Gordon LLP

[57] ABSTRACT

An artificial cotyloid socket having a domal outer shell (1) and a domal inner shell (2) subtending between them a cavity (3). Each of the outer and inner shells (1, 2) having a domal wall that merges into a rim (5, 6). The outer and inner shells are undetachably joined to each other at their rims (5, 6). The rim of the outer shell is reinforced and disposed relatively beneath a circle of merging (7). The circle of merging is defined by the intersection of the outer shell domal wall and the outer shell rim. A thickness of the wall continuously increases as one moves from a pole (4) of the outer shell toward the circle of merging (7).

14 Claims, 1 Drawing Sheet

ARTIFICIAL COTYLOID CAVITY

BACKGROUND OF THE INVENTION

1. Field of the Invention

The present invention generally relates to an artificial cotyloid socket having a domal outer shell and a domal inner shell subtending between them a cavity and, more particularly, to such an artificial cotyloid socket wherein the inner and outer shells are non-detachably secured to each other at their rims.

2. Description of Related Art

Spherical cotyloid sockets having inner and outer shells that are non-detachably secured to each other at their rims are especially well suited for cement-free implantation into the acetabulum.

The state of the art is represented by European patent document A 444,382. This publication discloses such a cotyloid socket in the form of a "monobloc" structure. Unfortunately, this design has the drawback that its outer shell is of constant wall thickness and is in a sandwich form. These features restrict elasticity. Suspension between the outer and inner shells must be controlled by an additionally installed spring system and, consequently, is not self-supporting.

SUMMARY OF THE INVENTION

An object of the invention is to remove or minimize the aforementioned drawbacks in the state of the art. The artificial cotyloid socket according to the present invention is increasingly elastic in a direction toward the (geographic) pole while nevertheless being simple and economical to manufacture.

In accordance with the present invention, the artificial cotyloid socket has a domal outer shell and a domal inner shell subtending between them a cavity. The inner and outer shells are joined to one another at their rims. The outer shell merges into a reinforced rim underneath a circle of merging, which is the intersection of the outer shell domal wall and the outer shell rim. The outer shell continuously increases in thickness as one moves from a pole of the outer shell toward the circle of merging.

The arrangement of the present invention offers the advantage of adequate mechanical stability in the direction of the resulting axis of stress while optimal elasticity and adaptability are provided in the region of the artificial cotyloid socket's pole. Accordingly, with the present invention, improved elasticity and adaptability are provided in the region where the implant attains its lowest point in the milled-out acetabulum.

The outer shell's wall thickness is less at its pole than at its latitude of 20 to 40 degrees (preferably 25 to 35 degrees), that is the approximate site where the elastic range of the invention begins and appropriately is less than 0.30 mm, preferably less than 0.25 mm at the pole. The wall thickness at 30 degree latitude is appropriately about 0.5 mm. Preferably, the outer shell's wall thickness is 30 to 60% of its wall thickness at its latitude of 30 degrees.

The rim of the outer shell is fitted with a specific shape and outside surface for anchoring in the bone. The conical rim shape allows primary clamping, technically called a "press fit", to prevent tipping. Non-rotatability is secured by axial rim grooves. The rim surface is salient in three dimensions. Such a structure is from 0.3 to 0.8 mm, preferably, 0.4 to 0.6 mm, to facilitate bone growth onto or into the prosthesis.

The outer shell may be made of pure titanium or a titanium alloy. The inner shell advantageously is made of one of the following materials: a cobalt-chromium-molybdenum alloy, a ceramic, polyethylene or carbon-fiber reinforced carbons.

In manufacture, a complete assortment with several cotyloid sockets of different sizes can be produced, identical inner shells being used for all cotyloid sockets and the different sizes being achieved by means of outer shells of different sizes.

Essentially the advantages of the invention may be considered being that the cotyloid socket of the invention allows:

1. matching anchoring and functionality to the physiological elasticity of the acetabulum,
2. a simply manufactured kit with minimal additional instrumentation, and hence
3. surgery can be carried out in simple and problem-minimizing manner.

BRIEF DESCRIPTION OF THE DRAWINGS

These and further features of the present invention will be apparent with reference to the following description and drawings, wherein.

DETAILED DESCRIPTION OF THE PREFERRED EMBODIMENTS

Figure 1:
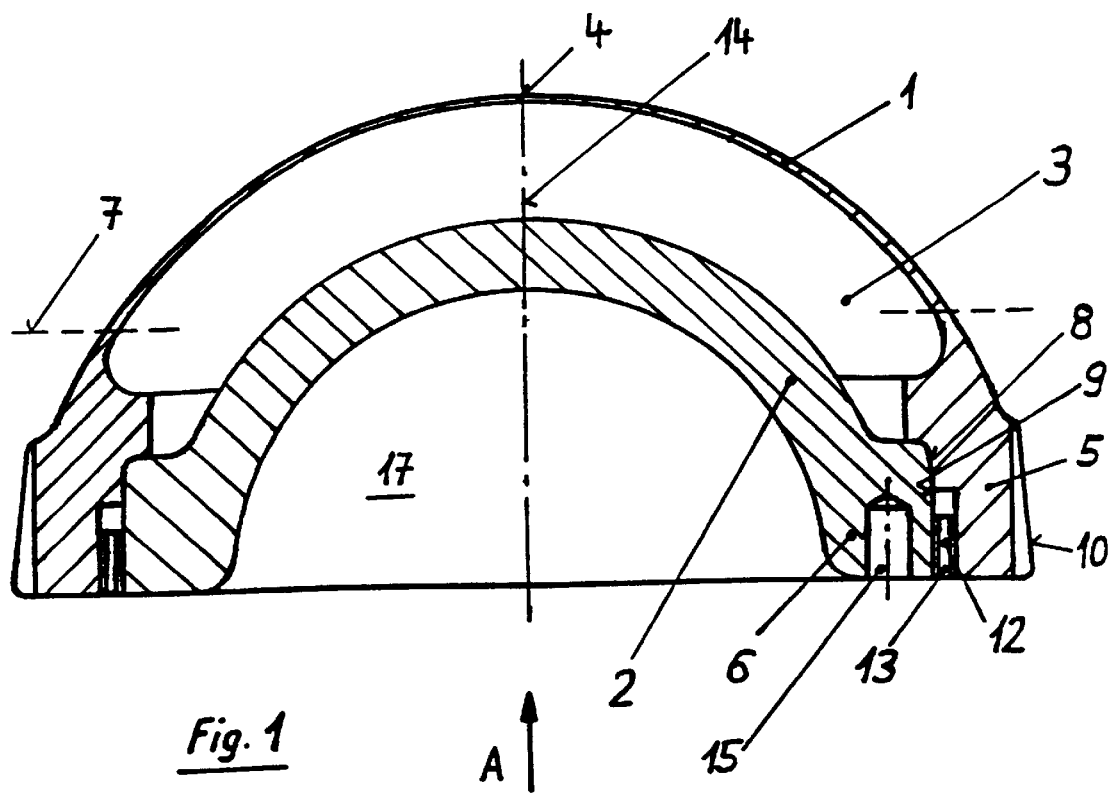
FIG. 1 is an enlarged cross-section through the axis of rotation of the cotyloid socket of the invention.
Figures 2, 3:
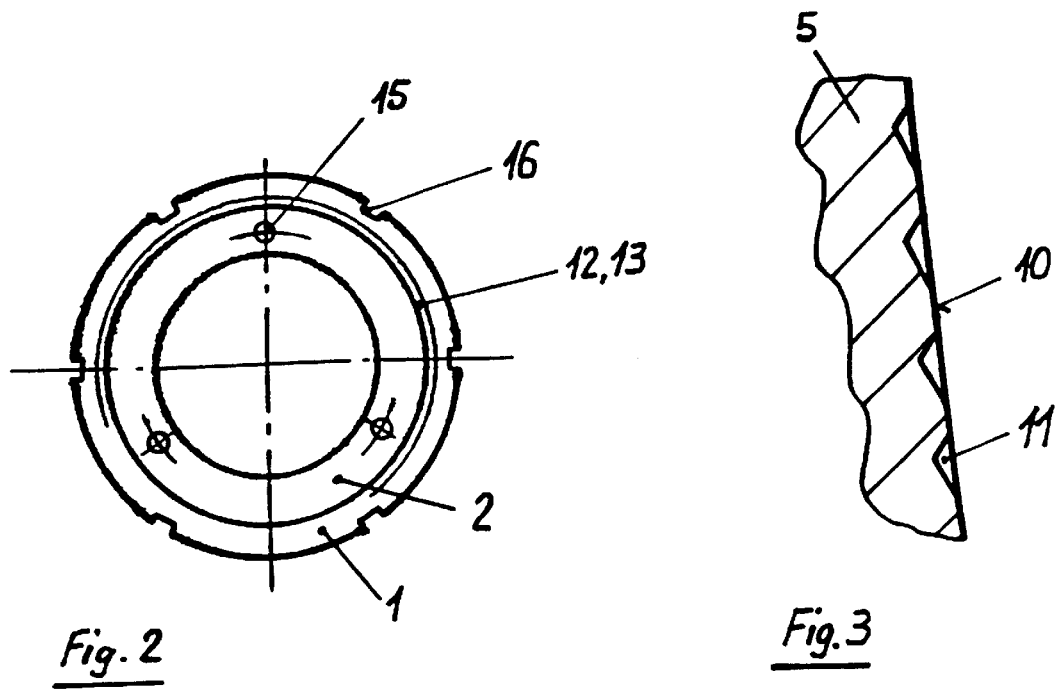
FIG. 2 is an actual-size view from below in the direction for the arrow A into the inside of the cotyloid socket of the invention shown in FIG. 1.
FIG. 3 is an enlarged cross-sectional detail in the vicinity of the outer rim of the cotyloid socket of FIG. 1.

The artificial cotyloid socket shown in FIGS. 1 and 2 consists of a domal outer shell 1 and a domal inner shell 2. The domal outer shell 1 has a reinforced rim 5 and an inside thread 12. The domal inner shell 2 has a rim 6 and an outside thread 13 forming a hemi-spherical inside space 17 to receive the head (not shown) of the femur portion of a hip prosthesis. The two shells 1, 2 are screwed together by their threads 12, 13 during the manufacture of the artificial cotyloid socket.

Furthermore, the rim 6 of the inner shell 2 comprises a conical outer surface 8. The rim 5 of the outer shell 1 comprises a conical inner surface 9. The conical outer surface 8 and conical inner surface 9 come together in mutual frictionally locking contact, as shown in FIG. 1, when the two shells are screwed together during manufacture. The threads 12, 13 may be rendered non-detachable or permanently affixed to one another by crimping, as a result of which the outer and inner shells 1, 2 are rigidly joined to one another at their rims 5, 6 and contain a cavity 3 impermeable to liquids and gases.

The wall thickness of the outer shell 1 at its pole 4 (geographic pole) is merely 0.2 mm and increases continuously to 0.5 mm at 30 degrees' latitude approximately.

As shown in FIGS. 1 and 2, the inner shell 2 is fitted with three blind holes 15 at its rim 6. The blind holes 15 run substantially parallel to the axis of rotation 14 of the cotyloid socket. The blind holes 15 are used to manipulate the cotyloid socket by means of an instrument (not shown) engaging them. Axial rim grooves 16 are configured along the conical outer surface 10.

As shown in FIG. 3, the reinforced, externally conical rim 5 of the outer shell 1 comprises an outer surface 10 that will rest against the bone. The outer surface 10 includes a three-dimensional structure 11 having a depth of 0.5 mm.

What is claimed is:

1. An artificial cotyloid socket having a domal outer shell (1) and a domal inner shell (2) subtending there between a cavity (3), each of said outer and inner shells (1, 2) having a domal wall that merges into a rim (5. 6), said outer and inner shells being undetachably joined to each other at said rims rims (5, 6), said outer shell rim (5) being reinforced and being disposed relatively beneath a circle of merging (7), said circle of merging being defined by the intersection of said outer shell domal wall and said outer shell rim, wherein a thickness of said wall continuously increases as one moves from a pole (4) of the outer shell toward the circle of merging (7).

2. Cotyloid socket as claimed in claim 1, wherein the circle of merging (7) is located between 20 to 40 degrees' latitude of said outer shell (1).

3. Cotyloid socket as claimed in claim 2, wherein the wall thickness of the outer shell (1) is less than 0.30 mm at said pole (4).

4. Cotyloid socket as claimed in claim 3, wherein the wall thickness of the outer shell (1) at said pole (4) is between about 30–60% of the wall thickness of the outer shell (1) at the circle of merging (7).

5. Cotyloid socket as claimed in claim 4, wherein the rim (5) of the outer shell (1) includes an inner surface having threads (12) formed thereon, said inner shell rim (6) including an outer surface having threads (13) formed thereon, said outer shell threads cooperating with said inner shell threads to permit said inner and outer shells to be threadably attached to one another.

6. Cotyloid socket as claimed in claim 5, wherein the rim (6) of the inner shell (2) comprises a conical outer surface (8) and the rim (5) of the outer shell (1) comprises a conical inner surface (9), said conical inner surface being connected in a frictionally-locking manner to the conical outer surface (8).

7. Cotyloid socket as claimed in claim 6, wherein the rim (5) of the outer shell (1) includes a conical outer surface (10), said outer shell conical outer surface being adapted for engagement with a bone and having axial rim grooves (16) and defining a three-dimensional structure (11).

8. Cotyloid socket as claimed in claim 7, wherein the three-dimensional structure (11) has a depth of between about 0.3 to 0.8 mm.

9. Cotyloid socket as claimed in claim 8, wherein the outer shell (1) is made of a material selected from the group consisting of: pure titanium and titanium alloy.

10. Cotyloid socket as claimed in claim 9, wherein the inner shell (2) is made of a material selected from the group consisting of: cobalt-chromium-molybdenum alloys, ceramics, polyethylene, and carbon-fiber reinforced carbons.

11. Cotyloid socket as claimed in claim 10, wherein the rim (6) of the inner shell (2) has at least three blind holes (15) formed therein, said holes extend substantially parallel to an axis of rotation (14) of the cotyloid socket.

12. Cotyloid socket as claimed in claim 2, wherein the circle of merging (7) is located between 25 to 35 degrees' latitude of said outer shell (1).

13. Cotyloid socket as claimed in claim 2, wherein the wall thickness of the outer shell (1) is less than 0.25 mm at said pole (4).

14. Cotyloid socket as claimed in claim 7, wherein the three-dimensional structure (11) has a depth of between about 0.4 to 0.6 mm.

* * * * *